US008976351B2

(12) United States Patent
Bivolaru et al.

(10) Patent No.: US 8,976,351 B2
(45) Date of Patent: Mar. 10, 2015

(54) SPATIALLY-AND TEMPORALLY-RESOLVED MULTI-PARAMETER INTERFEROMETRIC RAYLEIGH SCATTERING SYSTEM AND METHOD

(71) Applicants: The George Washington University, Washington, DC (US); The United States of America as represented by the Administrator of the National Aeronautics and Space Administration, Washington, DC (US)

(72) Inventors: Daniel Bivolaru, Hampton, VA (US); Andrew D. Cutler, Yorktown, VA (US); Paul M. Danehy, Newport News, VA (US)

(73) Assignees: The United States of America as Represented by NASA, Washington, DC (US); The George Washington University, Washington, DC (US); Daniel Bivolaru, Hampton, VA (US)

( * ) Notice: Subject to any disclaimer, the term of this patent is extended or adjusted under 35 U.S.C. 154(b) by 165 days.

(21) Appl. No.: 13/671,270

(22) Filed: Nov. 7, 2012

(65) Prior Publication Data
US 2013/0141721 A1 Jun. 6, 2013

Related U.S. Application Data

(63) Continuation of application No. PCT/US2011/035580, filed on May 6, 2011.

(60) Provisional application No. 61/424,502, filed on Dec. 17, 2010, provisional application No. 61/346,599, filed on May 20, 2010, provisional application No. 61/332,511, filed on May 7, 2010.

(51) Int. Cl.
*G01N 21/00* (2006.01)
*G01N 21/53* (2006.01)
(Continued)

(52) U.S. Cl.
CPC ............... *G01N 21/53* (2013.01); *G01N 21/72* (2013.01); *G01J 3/4412* (2013.01)
USPC ..................................................... 356/337

(58) Field of Classification Search
CPC ........... G01J 3/26; G01N 21/53; G01N 21/01; G01N 21/25; G01N 21/45
USPC ............................................ 356/337, 338, 341
See application file for complete search history.

(56) References Cited

U.S. PATENT DOCUMENTS

| 5,228,051 A | 7/1993 | Matthews |
| 7,106,447 B2 | 9/2006 | Hays |

(Continued)

OTHER PUBLICATIONS

D. Bivolaru, et al.; "Simultaneous CARS and Interferometric Rayleigh Scattering"; Review of Scientific Instruments, 22$^{nd}$ International Congress of Instrumentation in Aerospace Simulations Facilities; Jun. 2007; 8 pgs.

(Continued)

*Primary Examiner* — Jonathan Hansen
(74) *Attorney, Agent, or Firm* — Blank Rome LLP

(57) ABSTRACT

A system that simultaneously measures the translational temperature, bulk velocity, and density in gases by collecting, referencing, and analyzing nanosecond time-scale Rayleigh scattered light from molecules is described. A narrow-band pulsed laser source is used to probe two largely separated measurement locations, one of which is used for reference. The elastically scattered photons containing information from both measurement locations are collected at the same time and analyzed spectrally using a planar Fabry-Perot interferometer. A practical means of referencing the measurement of velocity using the laser frequency, and the density and temperature using the information from the reference measurement location maintained at constant properties is provided.

12 Claims, 8 Drawing Sheets

(51) Int. Cl.
*G01N 21/72* (2006.01)
*G01J 3/44* (2006.01)

(56) References Cited

U.S. PATENT DOCUMENTS

| | | | |
|---|---|---|---|
| 7,414,708 B2 | 8/2008 | Bivolaru et al. | |
| 7,505,145 B2 | 3/2009 | Hays et al. | |
| 8,233,508 B2* | 7/2012 | Mirov et al. | 372/20 |
| 8,269,971 B1* | 9/2012 | Marsh et al. | 356/437 |
| 2007/0165236 A1* | 7/2007 | Haridas | 356/451 |

OTHER PUBLICATIONS

R.A. Baurle; "Modeling of High Speed Reacting Flows: Established Practices and Future Challenges"; 42nd AIAA Aerospace Sciences Meeting and Exhibit; Jan. 8-8, 2004; AIAA 2004-0267, Reno, Nevada; 15 pgs.

D. Bivolaru, et al.; "Direct-View Multi-Point Two-Component Interferometric Rayleigh Scattering Velocimeter"; American Institute of Aeronautics and Astronautics; pp. 1-14; Jan. 9-12, 2008.

P.M. Danehy, et al.; "Simultaneous Temperature and Velocity Measurements in a Large-Scale, Supersonic, Heated Jet", Jun. 5-6, 2006; pp. 1-13.

R.W. Dibble, et al.: "An Improved Method of Data Aquistion and Reduction for Laser Raman-Rayleigh and Flourescence Scattering from Multispecies"; Applied Physics B; 1990; pp. 39-43: vol. 51; Springer-Verlag.

J.P. Drummond, et al.: "Development of Methods to Predict the Effects of Test Media in Ground-Based Propulsion Testing": NASA Langley Research Center: Jan. 6, 2009; pp. 1-111; ANSI Std.

J.P. Drummond, et al.; "Supersonic Combustion Research at NASA": 2007 Fall Technical Meeting Eastern States Section of the Combustion Institute University of Virginia; Oct. 21-27, 2007, 12 pgs.

F. Farassat, et al.; "The Acoustic Analog—A Powerful Tool in Aeroacoustics with Emphasis on Jet Noise Prediction"; American Institute of Aeronautics and Astronautics, NASA Langley Research Center, Hampton, VA; May 10-12, 2004; paper No. 2004-2872; 16 pgs.

S. Gordon. et al ; "Computer Program for Calculation of Complex Chemical Equilibrium Compositions and Applications"; NASA Reference Publication 1311; Oct. 1994: pp. 1-58.

R.D. Hancock, et al.; "Nitrogen and Hydrogen CARS Temperature Measurements in a Hydrogen/Air Flame Using a Near-Adiabalic Flat-Flame Burner"; Combustion and Flame; 1997; pp. 323-331; vol. 109; The Combustion Institute; Published by Elsevier Science Inc.

R.B. Miles, et al ; "Laser Rayleigh Scattering"; Measurement Science and Technology; 2001; pp. 33-51: vol. 12, Institute of Physics Publishing.

S.O. Byrne, et al.; "Dual-Pump Coherent Anti-Stokes Raman Scattering Measurements in a Supersonic Combustor"; AIAA Journal; Apr. 2007; pp. 922-933; vol. 45; No. 4.

S. Yip; "Rayleigh Scattering in Dilute Gases": The Journal of the Acoustical Society of America; Feb. 1970; pp. 941-949; vol. 49; No. 3 (Part 3).

* cited by examiner

US 8,976,351 B2

SPATIALLY- AND TEMPORALLY-RESOLVED MULTI-PARAMETER INTERFEROMETRIC RAYLEIGH SCATTERING SYSTEM AND METHOD

RELATED APPLICATIONS

The present application is a continuation of PCT Application No. PCT/US11/035580, filed May 6, 2011, which claims priority to U.S. Provisional Application Nos. 61/424,502, filed Dec. 17, 2010, 61/346,599, filed May 20, 2010, and 61/332,511, filed May 7, 2010, the contents of which are incorporated herein by reference.

STATEMENT REGARDING FEDERALLY SPONSORED RESEARCH OR DEVELOPMENT

This invention was made with government support under contracts NASW-99027, NNX07AC32A/2007 and NNX08AB31A/2008 awarded by NASA. The government has certain rights in the invention.

FIELD OF THE INVENTION

The present invention relates to spatially and temporally resolved multi-parameter Interferometric Rayleigh scattering.

BACKGROUND OF THE INVENTION

Molecular-based diagnostics techniques capable of obtaining simultaneous multiple fluid properties such as temperature, density and velocity are critically important for characterizing the flows within airbreathing engines, such as scramjet engines and scramjet-turbine combined cycle engines for hypervelocity vehicles. At the other end of the velocity range, such techniques are needed to help in the development of the next generation of subsonic, low noise aircraft. Statistical correlations between these properties will lead to a more detailed understanding of the complex flow behavior as well as aid in the development of new turbulence models for scramjet engine flow path designs, and more accurate aircraft noise prediction tools. Required are instantaneous and simultaneous measurements of temperature, velocity, density, pressure, and chemical composition at multiple points in a gas when the spatial (hundreds of microns or less) and temporal (hundreds of nanoseconds or less) scales of the turbulent fluctuations are resolved. Specifically of interest are the mean properties and their turbulent variances and co-variances as well as the probability density functions. To date, diagnostics techniques to meet all these requirements on a single platform do not exist, but many linear and non-linear optical techniques are available for partial achievement of this goal. One of these linear techniques, the Interferometric Rayleigh Scattering technique (IRS) (discussed in Bivolaru, D., Danehy, P. M., Gaffney, Jr. R. L., and Cutler, A. D., "Direct-View Multi-Point Two-Component Interferometric Rayleigh Scattering Velocimeter," AIAA-2008-0236, 46th Aerospace Sciences Meeting, Reno, Nev., Jan. 9-12, 2008), has been used for low-as well as for high-speed supersonic/hypersonic non-reacting and combusting flows yielding temporally and spatially resolved simultaneous measurements of two-components of bulk velocity.

Recent efforts have attempted to obtain the ro-vibrational temperature, and the species content of N2 and O2 from measurements with CARS (coherent anti-Stokes Raman spectroscopy), simultaneously with velocity with IRS. Those efforts include Danehy, P. M., Magnotti, G., Bivolaru, D., Tedder, S., and Cutler, A. D., "Simultaneous Temperature and Velocity Measurements in a Large-scale, Supersonic, Heated Jet," Paper 1193, 55th JANNAF Propulsion Meeting, Boston, Mass., May 12-16, 2008. Also, Bivolaru, D., Lee, J. W., Jones, S. B., Tedder, S., Danehy, P. M., Weikl, M. C., Magnotti, G., and Cutler, A. D., "Mobile Rayleigh—CARS Instrument for Simultaneous Spectroscopic Measurement of Multiple Properties in Gaseous Flows," 22nd International Congress on Instrumentation in Aerospace Simulations Facilities (ICIASF), Monterey, Calif., June, 2007; and Bivolaru, D, Danehy, P. M., Grinstead, K. D., Jr., Tedder, S., and Cutler, A. D., "Simultaneous CARS and Interferometric Rayleigh Scattering," AIAA-2006-2968, 25th AIAA Aerodynamic Measurement Technology and Ground Testing Conference, San Francisco, Calif., Jun. 5-8, 2006. However, this work needs improvements in instrument precision, as well as additional simultaneous measurements, the gas density and a measurement of translational temperature from IRS.

SUMMARY OF THE INVENTION

Accordingly, it is an object of the invention to provide a multi-parameter IRS technique for simultaneously obtaining the translational temperature, the bulk velocity, and the density in gases at elevated temperatures in a non-intrusive manner. In one non-limiting illustrative embodiment, the invention measures these properties in a $H_2$-air combustion flame (Hencken burner), relative to simultaneous measurements in a reference $N_2$-filled cell. The measurements are compared with the adiabatic flame theory predictions and the applicability of this method to turbulent flows is discussed.

In accordance with these and other objectives, a system is provided which simultaneously measures the translational temperature, bulk velocity, and density in gases by collecting, referencing, and analyzing nanosecond time-scale Rayleigh scattered light from molecules. A narrow-band pulsed laser source is used to probe two largely separated measurement locations, one of which is used for reference. The elastically scattered photons containing information from both measurement locations are collected at the same time and analyzed spectrally using a planar Fabry-Perot interferometer. A practical means of referencing the measurement of velocity using the laser frequency, and the density and temperature using the information from the reference measurement location maintained at constant properties is described. A simplified Gaussian distribution model to the scattered light spectra is used to obtain the flame properties. Corrections to this model are applied at lower gas temperatures when the simplified Gaussian approximation is no longer suitable. The near-zero measured velocity as a function of the measured flame temperature, and a comparison of the measured flame density and temperature with the perfect gas law are presented.

These and other objects of the invention, as well as many of the intended advantages thereof, will become more readily apparent when reference is made to the following description, taken in conjunction with the accompanying drawings.

DP-Dove prism; F-Pi-Fabry-Perot interferometer; em-CCD-electron avalanche multiplication CCD camera; mv-measurement volume.

Figure 2:
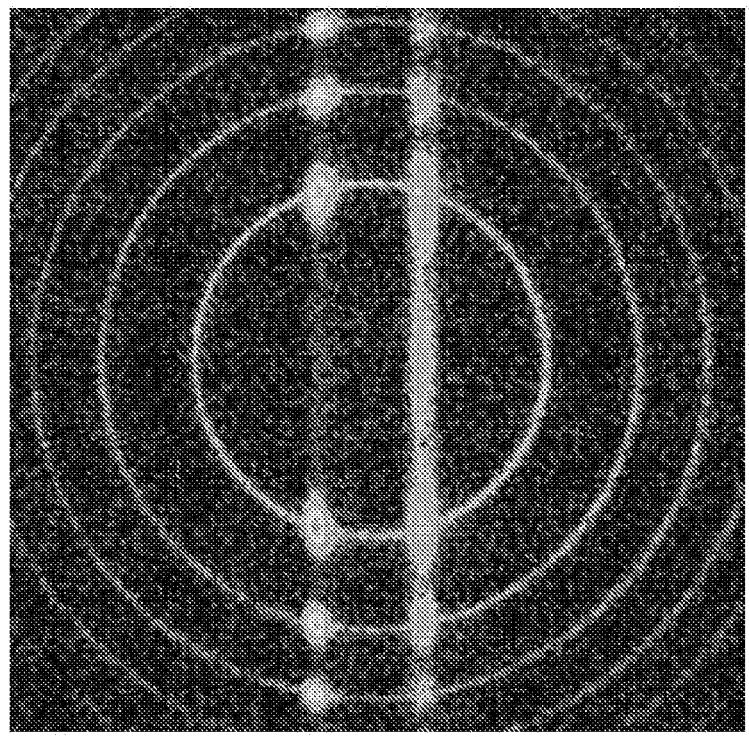
Figure 2:
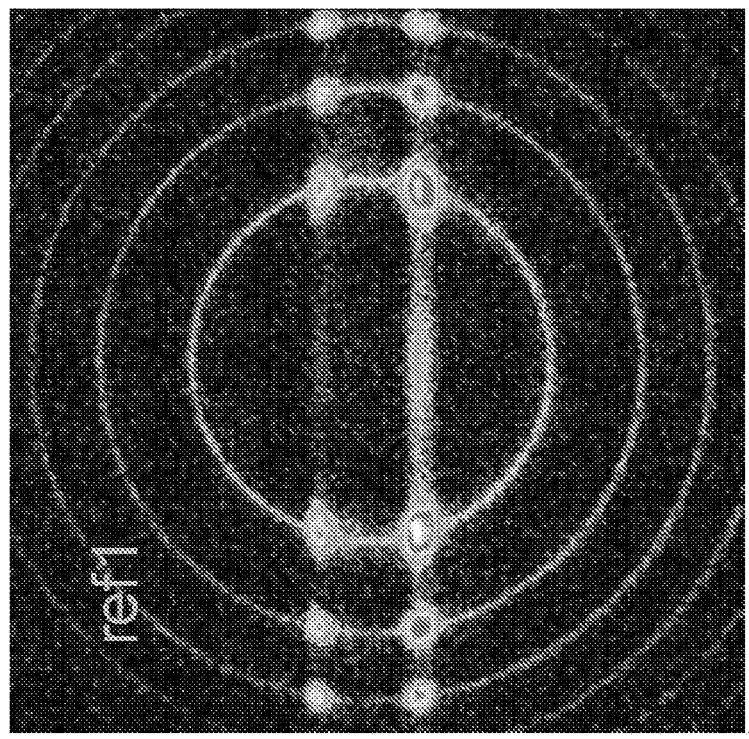

FIG. 2 shows Fabry-Perot interferograms containing multiple signals of elastically scattered light from two largely separated measurement locations, one of which is used for reference. The bottom horizontal pattern (exp1) is the signal obtained at the location of a $H_2$-air Hencken burner flame: (a), in air at 293 K outside the flame, and (b), in the flame at about 1560 K. The top horizontal pattern (exp2) is the signal from the secondary measurement location situated in a low-pressure $N_2$ gas cell at room temperature. This signal is used to reference the measurement of temperature and density performed at the flame location. The concentric ring pattern (ref1) is the spectra of unshifted laser light used to reference the Doppler frequency of all signals and facilitate computation of the gas bulk velocity at both locations.

Figure 3:
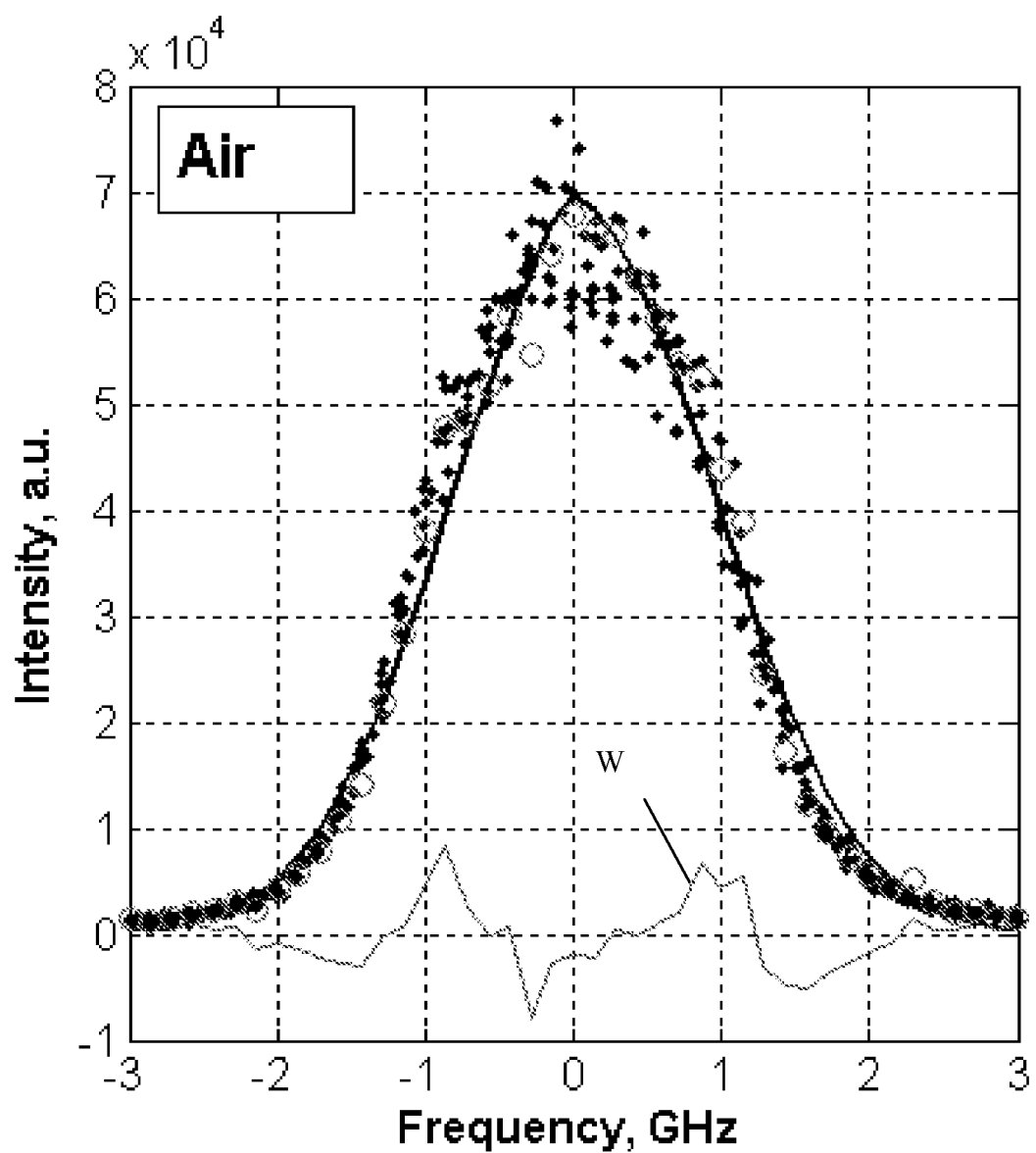

FIG. 3 shows the combined Rayleigh and laser spectra obtained, (a), in atmospheric air at ~293 K, and (b), in $H_2$-air flame at $\phi$~0.5 (1637 K). The intensity scale is shown in arbitrary units (a.u.). Data contain ten instantaneous measurements to emphasize the trend (solid circles). Only one dataset (empty circles) is fit with a combined Gaussian-Lorenzian function (solid black line). The residual of the fit is shown with a line W.

Figure 4:
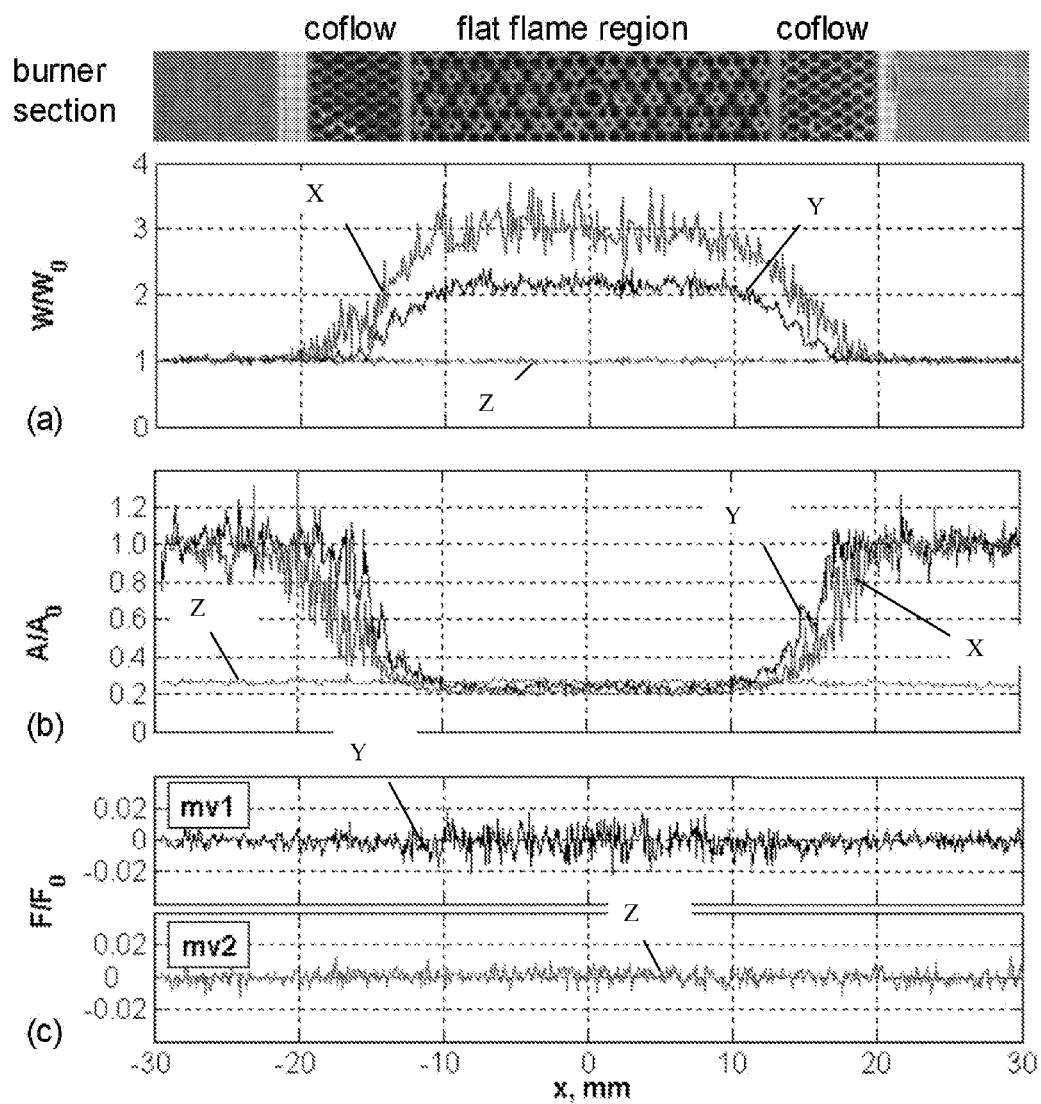

FIG. 4 is a chart showing normalized spectral properties obtained simultaneously in H2-air Hencken burner flame ($\phi$~1.0, and $\phi$~0.5), and in the reference N2-cell relative to atmospheric properties: (a), the spectral bandwidth, (b), the area of the spectra, and (c), the Doppler shift frequency. The inset on the top of the figure is a top view of the central section of the burner.

FIG. 5(a) is the measured gas density in air and in flame as a function of the measured temperature, compared with the perfect gas law (solid curve). FIG. 5(b) is the measured bulk velocity in air and in flame as a function of the measured temperature. The gas density and temperature are normalized with respect to the ambient air density (1.2 kg/m3) and temperature (293.5 K), respectively. The velocity is normalized by the maximum measurable velocity (3 km/s). Data obtained at atmospheric pressure during a full scan through a $H_2$-air Hencken burner flame at about $\phi$=0.5. The burner stabilization co-flow is nitrogen gas.

Figure 6:
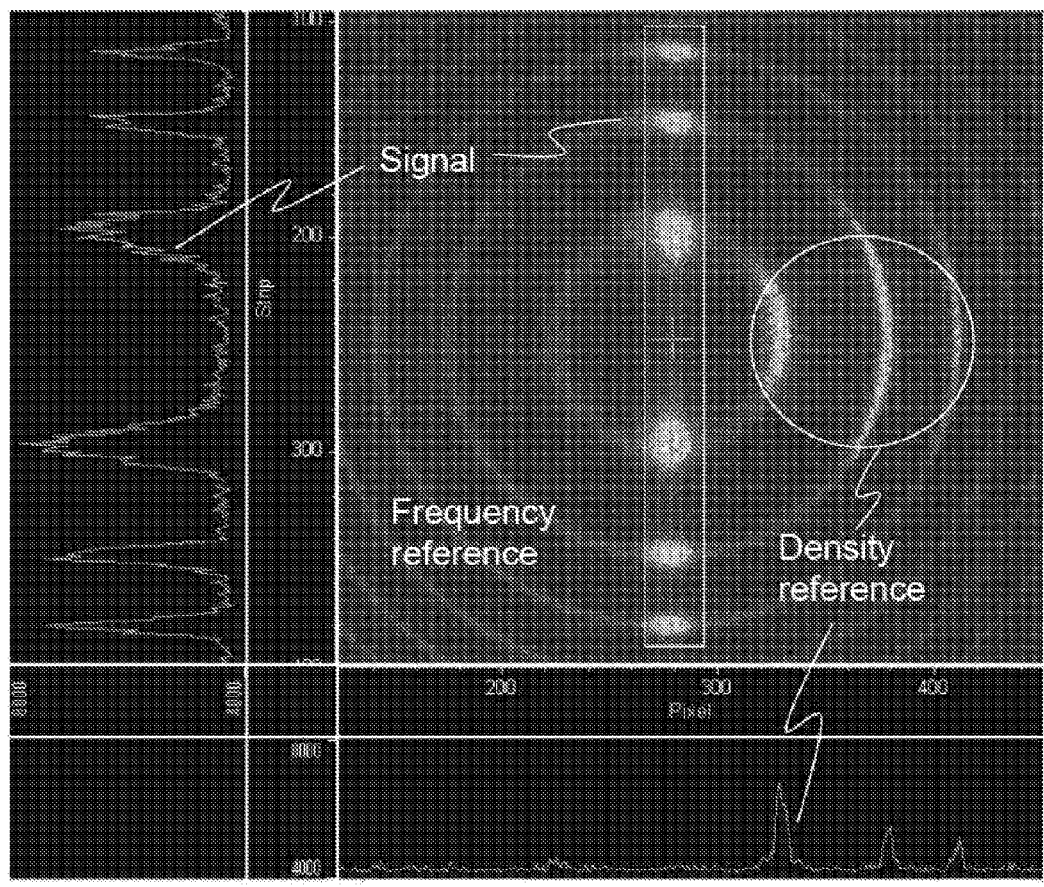

FIG. 6 is a combined single-shot interferogram of signal (horizontal pattern), frequency reference (concentric ring pattern), and density reference from an optical fiber (semi-circular pattern).

Figure 7:
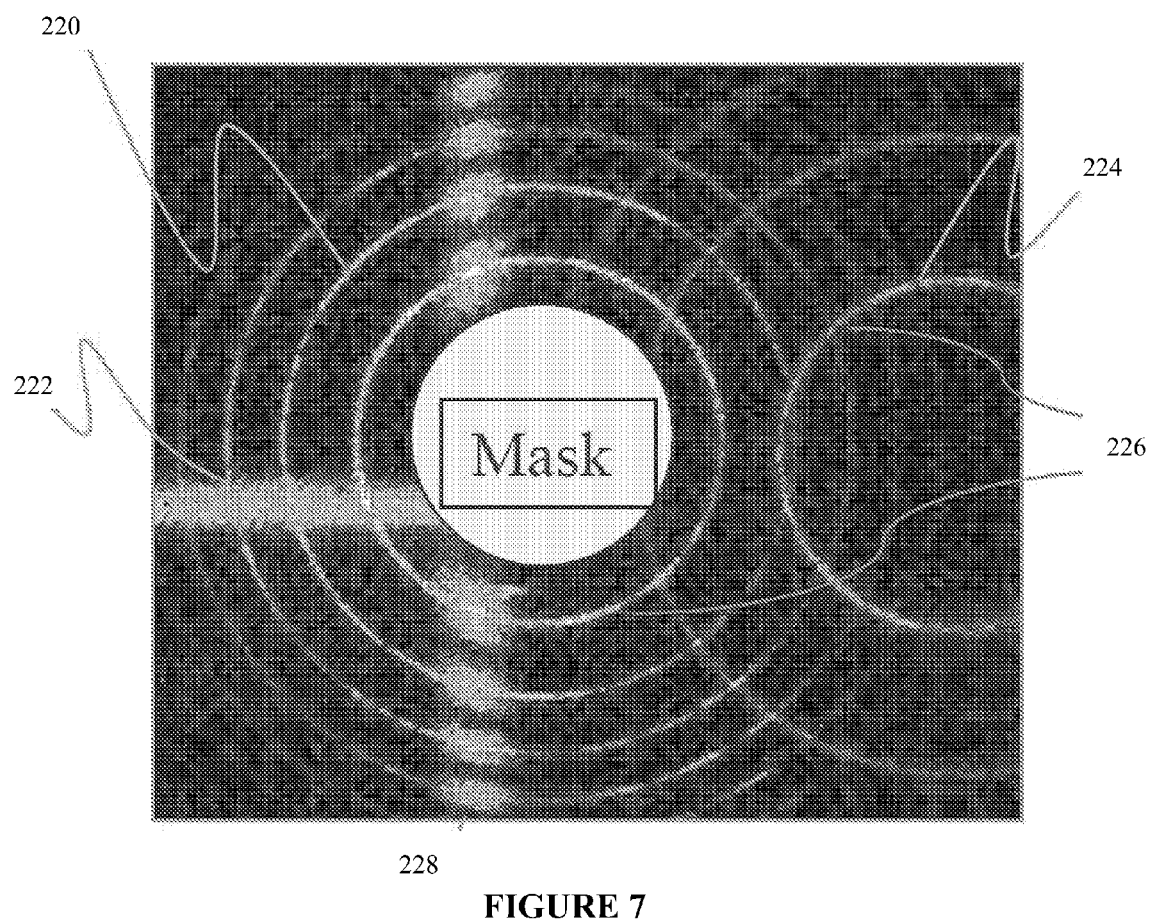

FIG. 7 is an instantaneous image containing two interferograms of different spectral resolutions.

DETAILED DESCRIPTION OF THE PREFERRED EMBODIMENTS

In describing the preferred embodiments of the present invention illustrated in the drawings, specific terminology is resorted to for the sake of clarity. However, the present invention is not intended to be limited to the specific terms so selected, and it is to be understood that each specific term includes all technical equivalents that operate in a similar manner to accomplish a similar purpose.

The interferometric Rayleigh scattering (IRS) technique uses a narrow-band polarized laser source of wavelength $\lambda_0$ for probing gas molecules situated at a given measurement volume through photon scattering. Both elastic Rayleigh and inelastic Raman scattering of photons occurs. The inelastic scattering arises from changes in the rotational and vibrational states of the molecules during the scattering process. This process is weak and occurs in a different wavelength band than the laser wavelength. The Rayleigh scattering process is directly related to the spatio-temporal motion of the gas molecules and does not change the internal energy of the molecules. It is orders of magnitude stronger and occurs near the laser wavelength. The number of photons scattered are proportional to the incident laser energy. Receiving optics directly collect the scattered light (near $\lambda_0$) in a small solid angle, optically compare it with laser light for frequency reference, and analyze it spectrally with a high-resolution Fabry-Perot interferometer and a CCD camera detector.

The details of the spectral structure are related to the state of collisions between gas molecules traditionally divided in two regimes: hydrodynamic or collision dominated, and kinetic or collisionless regime (Rayleigh regime), without a clear border between them. The shape of the spectra is related to a non-dimensional ordering parameter y=$\alpha$/K$\alpha$, where $\alpha$=p/$\mu$ is the collision frequency (p is the gas pressure and $\mu$ is the shear viscosity) and K$\alpha$ is the acoustic spatial frequency (K is the magnitude of the resultant wave vector K and $\alpha$ is the speed of sound). For "s" type scattering, the angle between the electric field vector E of the incident light of wave vector $k_0$ (vertically polarized) and the direction of the scattered light of wave vector $k_s$ (horizontal direction) is $\beta$=90°. The scattering angle $\theta$ is the angle between the direction of $k_0$ vector and the direction of $k_s$ vector along the optical axis of the receiving optics.

With these notations the resultant wave vector is $K=k_s-k_0$. Assuming that the wave vectors magnitudes are about the same $|k_s|\approx|k_0|$, the magnitude of the resultant wave vector is $$K=2k_0 \sin(\theta/2) \quad (1)$$

where $k_0=|k_0|=2\pi/\lambda_0$. For very low density gases y is negligibly small and the Rayleigh spectra is approximated with a Gaussian shaped spectra. For moderate density gases, when collisions between molecules start to dominate (y~1), the spectra include a central peak (Rayleigh) and two Lorentzian-shaped sidebands (acoustic scattering or Brillouin). The Rayleigh contribution arrives from thermal fluctuations dissipating by thermal conduction. For large ordering parameters, the line width in frequency is given by $D_T K^2$, where $D_T$ is the thermal diffusivity. The Brillouin sidebands are symmetrically Doppler shifted about the central Rayleigh peak due to acoustic scattering from small pressure fluctuations in the gas (propagating at the speed of sound). They are located at $\pm Ka/2\pi$, and their line width is given by $\Gamma K^2$, where $\Gamma$ is the sound attenuation coefficient. Then, the ratio of Rayleigh to Brillouin integrated intensities is ($\gamma-1$), where $\gamma$ is the ratio of specific heats. This approximation fails in the kinetic regime when y is negligibly small.

At elevated temperatures for atmospheric pressure (or low pressures at room temperature) (y<<1), if we neglect the acoustic Brillouin scattering, the velocity distribution of molecules is Maxwellian. For one velocity component this is given by $$f(\zeta)=(\pi w_\zeta)^{-1/2}\exp(-(\zeta-v)^2/w_\zeta^2) \quad (2)$$

where $\zeta$ is the velocity of a molecule, v is the bulk velocity of molecules, $$w_\zeta=(2k_B T/m)^{1/2} \quad (3)$$

is the full width at 1/e height of distribution f($\zeta$), T is the gas temperature, $k_B$ is the Boltzmann constant, and m is the molecular mass. The bulk velocity v is what is observed at macroscopic scale. For a gas at rest the bulk velocity is zero and the average molecular random velocity u=($\zeta$-v) due to deviations of $\zeta$ from v is also zero.

Photons of frequency $\upsilon$ from the incident probing beam are scattered from molecules moving in all directions with the random velocity u, and are shifted in frequency according to the Doppler effect $$d\upsilon=(\upsilon-\upsilon_0)=(K\bullet u)/2\pi \quad (4)$$

Therefore, for a component of velocity along the resultant wave vector K one can relate the velocity distribution of the molecules to the scattered light frequency by rewriting Eq. (2) as $$f(\upsilon)=(\pi w)^{-1/2}\exp(-(d\upsilon/w)^2), \quad (5)$$

where the new spectral width in frequency is $$w=(2k_BT/m)^{1/2}\sin(\theta/2)/\lambda_0. \quad (6)$$

In a gas mixture (as for example in air or in a flame) the spectral distribution of the scattered light is a sum of distribution with contributions from each molecular species i weighted by their molar fraction $\chi_i$, and the differential scattering cross-section $\sigma_i$. Therefore one can write $$I(\upsilon) = CI_0 N \sum_{i=1}^{N_i} \chi_i \sigma_i f_i(\upsilon), \quad (7)$$

where $I_0$ is the laser intensity, and N is the total gas number density. The constant of proportionality C depends on the laser polarization, and wavelength; the size of the probe volume; and the solid angle of the light collection optics (collecting power), the collection direction, and the detector quantum efficiency.

To determine the gas properties, the scattered light spectra and the laser spectra are analyzed with theoretical models by least-square fitting techniques using the laser spectra as reference for Doppler shift calculations. Research efforts to extract the properties of gases by analyzing the spectra of scattered light with Fabry-Perot interferometers include in diluted gases, in low-speed combustion flames, and in high-speed rocket external flows. The use of kinetic models to obtain spectral information requires prior knowledge of gas parameters (that are not measured by the instrument) such as the internal specific heat per molecule, the ratio of shear to bulk viscosity, and the ratio of shear viscosity to thermal conductivity. This model is difficult to use since these parameters are not precisely known and there is limited data available for the species and range of temperatures required for measurements. In this work a simplified Gaussian-Lorentzian analytical model is used, easy to apply to the data, instead of a more detailed computational Rayleigh-Brillouin kinetic model. Then, corrections of these measured quantities via calibrations are applied to obtain quantitative information within an acceptable margin of error as it will be shown later.

Figure 1:
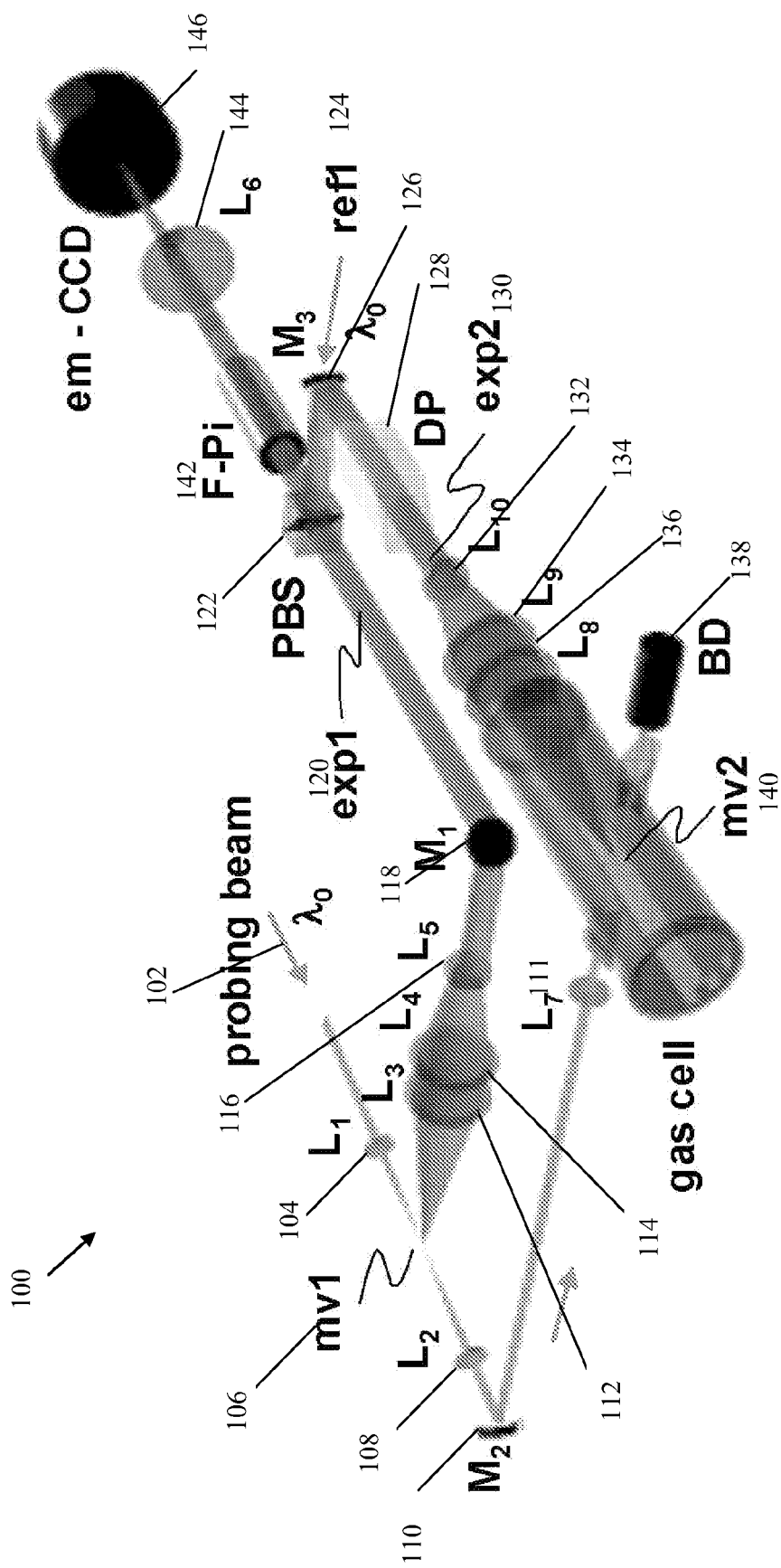
FIG. 1 shows the instrument configuration for simultaneous multi-point measurement of velocity, the gas translational temperature, and density at two largely-separated spatial locations. Legend: L-lens; M-planar mirror; BD-beam dump; PBS-polarization dependent beam splitter/combiner.

FIG. 1 is a non-limiting embodiment of the instrument design in accordance with a preferred embodiment of the invention. The system 100 references all measurable properties, the velocity, the temperature, and the gas density. This is performed with an optical setup that simultaneously records the spectral properties of Rayleigh scattered light from two largely separated measurement locations, one of which is used for reference. To increase the incident laser energy probing the measurement volume, and implicitly to increase the scattered signal, this system uses for probing two collinear laser beams slightly delayed in time for probing the gas sample. The laser source is a seeded dual Nd:YAG laser, with a wavelength, $\lambda_0$, of 532 nm, variable timing between pulses, 10 Hz repetition rate, nine nanoseconds pulse width and 0.005 cm$^{-1}$ bandwidth.

As shown, the probing laser beam (of wave vector $k_0$) 102 is focused at the measurement volume (mv1) 106 by the $L_1$ lens 104 and collected and re-collimated for further use by the $L_2$ lens 108. The L7 lens refocuses the recovered laser beam after passing through mv1 to generate the second measurement volume mv2. Thereafter, the remaining beam energy is lost in the beam dump BD. The elastically scattered light pulse (exp1) (of wave vector $k_s$) 120 is collected and collimated from the measurement volume mv1 106 by the $L_3$ lens 112 (which can have an f/4, 250-mm focal length, and is located 250 mm from the measurement volume mv1 106). The beam diameter of this signal is reduced to match the analyzing optics aperture diameter (~15 mm) using the beam reducer/expander formed by lenses $L_4$ 114 and $L_5$ 116, and directed using the mirror $M_1$ 118 toward the polarization dependent beam combiner PBS 122. The beam combiner PBS 122 facilitates the optical mixing of the signal with the un-scattered light (ref1) 124 used for frequency referencing.

In the present configuration, the polarization dependent beam combiner PBS 122 is used to also combine this beam (exp1) 120 with a second beam (exp2) 130 collected by the $L_8$ lens 136 from a secondary measurement volume mv2 140. This measurement volume 140 is located in a gas cell with known gas properties that is used for properties referencing as will be shown later. Similarly, this beam (exp2) 130 is reduced and collimated by the lenses $L_9$ 134 and $L_{10}$ 132, and directed by mirror $M_3$ 126 toward the combiner PBS 122. The light polarization of both signals is adjusted (not shown) such that the PBS 122 reflects the second beam exp2 130 together with the transmitted main beam 120 toward the Fabry-Perot interferometer (F-Pi) 142. The reference laser light 124 needed for frequency referencing is optically mixed with the signals at the PBS 122 by passing un-shifted laser light through the mirror $M_3$ 126 (or any other mirror, such as mirror $M_1$ 118. Therefore the interferogram formed by the F-Pi interferometer 142 and imaged by the $L_6$ lens 144 on the CCD camera 146 contains the spectra of exp1 120, exp2 130, and ref1 124.

FIG. 2 shows examples of interferograms containing multiple Rayleigh signals (exp1 and exp2) obtained in the cell (top horizontal pattern) and at the flame location (bottom horizontal pattern), in room air (293 K in FIG. 2(a)) before flame ignition, and in an H$_2$-air flame at equivalence ratio $\phi$=0.5(1560 K in FIG. 2(b)), respectively. The circular pattern is the interferogram of the laser light used for frequency reference (ref1). To avoid the eventual overlap of the closely spaced spectra exp1 and exp2 the pattern of exp2 could also be rotated in the image plane (for example by 90° or any other angle) using the Dove prism DP 128.

As mentioned earlier, in this arrangement the energy deposited at the measurement volumes is increased by spatially overlapping the two collinear laser beams slightly delayed in time. Additionally optical aberrations are introduced in the optical path of the focusing lens through lens tilting. This beam shaping is achieved by tilting the focusing lens $L_1$ slightly, 5° to 22° depending on the laser energy, and thereby introducing an astigmatism aberration of the beams at their foci. The tilting is performed about an axis perpendicular to the plane containing the incident laser beam and the signal collection direction. The elliptical beam allows more energy to be deposited in the flow without gas breakdown. This results in larger Rayleigh signal intensity if collected from a direction in the plane of the beam and the major axis of the ellipse, at the cost of reduced spatial resolution in the other dimension. In the experiments reported here a total of 385 mJ in two laser pulses separated in time by about 200 nanoseconds and a ratio of major to minor axis of the elliptical beam of about 10 at its first focus were used. The measurement volume is about 0.05 mm×0.2 mm×0.5 mm.

Both $L_3$ and $L_8$ lenses 112, 136 collect scattered light from the measurement locations at an angle $\theta=90°$ with respect to the corresponding probing laser beam direction. The Fabry-Perot interferometer 142 is made of solid glass with a free spectral range (FSR) of 8 GHz and a total finesse of about 22. This defines the maximum measurable Doppler shift and therefore the dynamic range for measuring velocities to about ±1.5 km/s when no prior velocity direction is known, or to about 3 km/s if the velocity direction is known. The range of measurable temperatures and densities in gases is from cryogenic temperatures to about 2500 K (limited at high temperatures by the overlap of consecutive orders of interference), and from 0.1 kg/m$^3$ to about 2 kg/m$^3$ (limited by the CCD dynamic range), respectively.

A non-limiting example of the invention is discussed to illustrate the invention. The first measurement location is situated in a non-premixed near-adiabatic $H_2$-air Hencken burner flame at atmospheric pressure (also used to calibrate the CARS measurements). The burner is placed vertically at the first measurement volume (mv1) in a direction perpendicular to the scattering plane. The hydrogen fuel and the air oxidizer are assumed to mix immediately above the burner surface. The burner surface is a 25.4 mm×25.4 mm rectangular section of hypodermic needle tubes for fuel and honeycomb passages for oxidant surrounded by a rectangular region of co-flow honeycomb design (a total of 36.5 mm×36.5 mm square surface). The $H_2$ and air equivalence ratio $\phi$ is varied from 0.1 to 1, by varying the flow rates (up to 0.5 l/sec). A constant flow of $N_2$ of 0.4 l/sec was directed through the co-flow nozzle at all fuel-air mixtures to improve flame stability and provide an almost dust-free environment for the instrument. The molecular content in the co-flow-flame interface is considered unknown. The flame temperature and species molar fractions in the flame region were calculated from the adiabatic flame theory.

The primary species are $N_2$, $O_2$, $H_2O$, and $H_2$, with the minor species (Ar, CO, OH, etc.) being neglected. The main product of combustion is water ($H_2O$) is in the gaseous state with negligible contribution from condensate. The perfect-gas law for the mixture is $p/\rho=(R/m)T$, where m is the molecular weight of the mixture (kg/kmole), p is the gas pressure (N/m$^2$), $\rho$ is the density (kg/m$^3$), and T is the gas temperature (K), and the perfect-gas constant R is 8314.5 J/(kmole)(K). The experiments are performed in room air ($m_{air}$=28.97 kg/kmole) at the atmospheric pressure $p_{air}$ (101324.72 N/m$^2$), temperature $T_{air}$ (293.5 K), and density $\rho_{air}$ (1.2 kg/m$^3$). The axial velocity of the flow (vertical direction) was estimated from flow rates at room temperature to about 10 m/sec, but higher velocities of this order of magnitude are expected during combustion. The radial velocity component (horizontal direction, measured in this experiment) is considered to be much smaller than the axial velocity (near zero).

The second measurement volume is situated in a constant properties glass cell containing $N_2$ at room temperature (293.5 K). The glass cell is connected with manual valves and plastic tubing to a feedstock of $N_2$ gas and to a vacuum pump. The initial air in the cell is removed with the vacuum pump and the $N_2$ is let in to the desired pressure before measurements. A pressure of $p_0$=26.5 kPa (198.5 torr) was used for the reported experiments. Lower pressure was used to ensure that the density and the y-parameter are similar to those in the combustion flow, which made the signals from both channels comparable.

Verification of the instrument is performed by obtaining all scattered light spectral properties simultaneously in the atmospheric flame and nitrogen ($N_2$) cell. Single-shot spectra $1(\upsilon)$ obtained in the air and $H_2$-air flame are shown in FIG. 3. The data are shown with solid and empty circles. The best fit to the data shown with empty circles using the sum of a Gaussian function for the scattered spectra and a Lorentzian function for the reference laser spectra is shown with a continuous line. Ten single-shot spectra are overlapped to the fitted data (solid circles) to emphasize the trend.

Figure 3B:
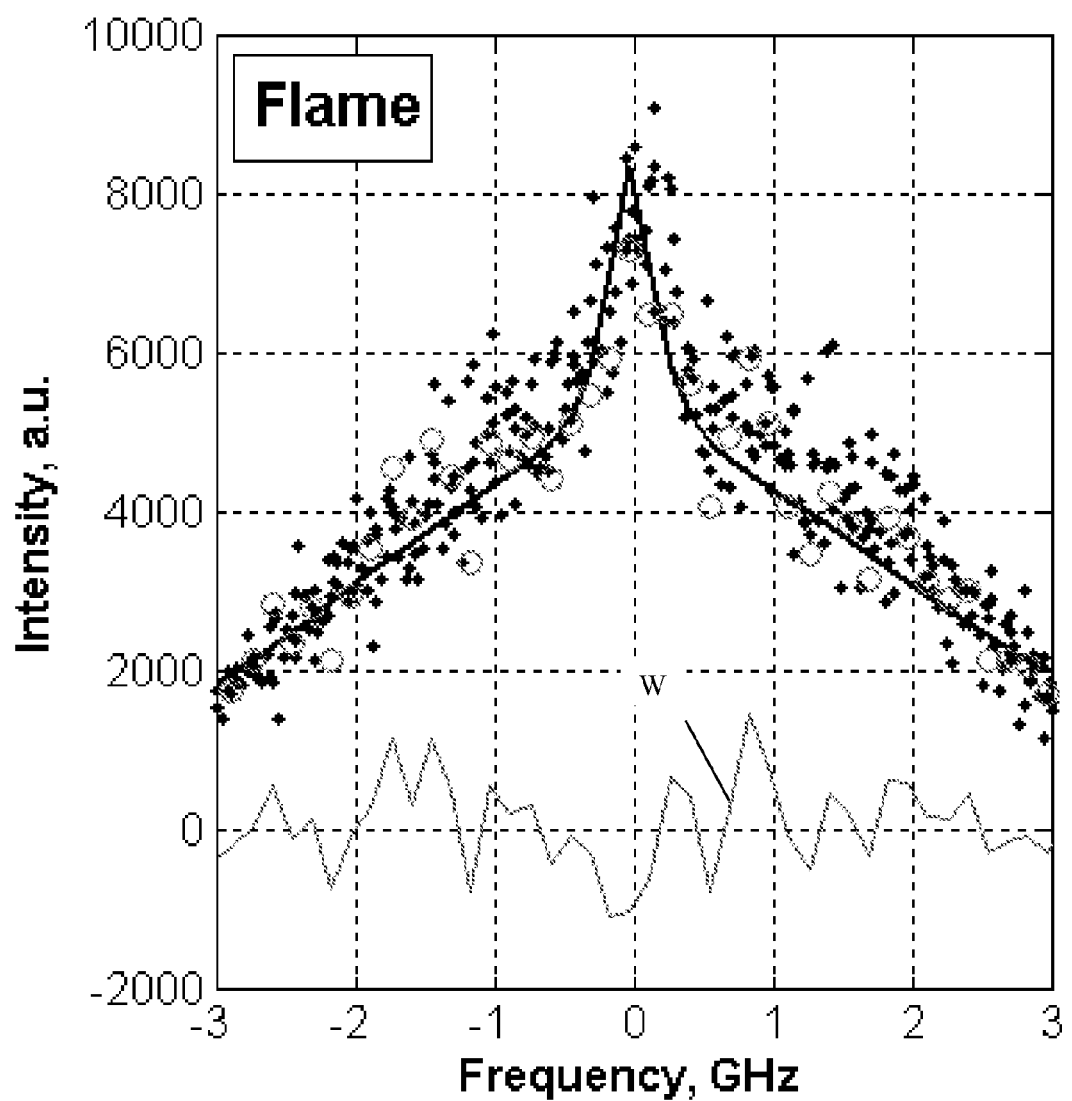

FIG. 3(a), and FIG. 3(b), show the spectra obtained in atmospheric air at the conditions described earlier, and in the flame at $\phi$=0.5 (~1637 K), respectively. The energy of the laser was maintained approximately constant during these measurements though any variations in laser intensity would be corrected by the data obtained in the reference cell. The parameter y for air at atmospheric conditions is 0.8 so the spectra in FIG. 3(a) should theoretically contain Brillouin sidebands Doppler shifted by about ±0.9 GHz around the Rayleigh center peak. The residual between the experimental data and the Gaussian fit is shown in the plot at the bottom of the figure (curve designed W). This indicates that the Gaussian fit function over-predicts the wings and under-predicts the top half of the distribution. Therefore the distinctive maxima of this residual function approximately detect the Brillouin peaks locations and the integral of its absolute value approximately shows the acoustic scattering contribution to the spectra. A theoretical analysis of this integral function of the y-parameter, shows that this contribution to the measured Rayleigh spectra is percentwise similar with the one found experimentally by Cattolica et al. ("The Interpretation of Spectral Structure of Rayleigh Scattered Light from Combustion Gases," AIAA-1976-0031, 14$^{th}$ Aerospace Sciences Meeting, Washington, D.C., January 267-28, 1976) for different gases. This relation is used to correct the measured spectra for the Brillouin contribution at lower gas temperatures.

For a Gaussian profile, the gas translational temperature is calculated from the spectral width. Normalizing Eq. (3) with respect to the known values of properties, the non-dimensional gas translational temperature becomes $T_m=W_m^2 m$, where $W_m$ is the measured non-dimensional width of the spectral profile, and m the molecular weight of the gas, which is a function of the gas composition, normalized by the molecular weight of air. This relation holds at moderate to high temperatures, but generates large errors without knowing the gas composition, and when the spectral profile deviates from a Gaussian function as described earlier. Since the molecular weight is not measured, it was estimated by comparing the measured width with the computed spectral width, which is a function of the molecular weight of the gas (and temperature). Then, the computed molecular weight of the gas is used as an approximation of the molecular weight of the gas existing at the time of measurement. In doing so it is assumed that for certain measured spectral widths only a small range of molecular weights are possible. For example, in the calculation of $T_m$, from the spectra shown in FIG. 3, the broadest Rayleigh spectra shown in FIG. 3(b) cannot be attributed to cold gases (higher molecular weights) that will produce the spectra shown in FIG. 3(a). The maximum error possible in these computations without considering this approximation of the molecular weight is about 16% in the whole range of measurable temperatures presented here. The actual error of the measurement obtained by estimating molecular weights as explained in this approximation is considered to be only a fraction of this maximum error.

To obtain the bulk velocity of the gas, the spectra are analyzed for the average spectral shift frequency relative to the laser spectra. From Eq. 4, if all molecules move with the bulk velocity v, the spectra is Doppler shifted from the laser frequency $v_0$ by $(v-v_0)/v_0 = 2(v/c)\sin(\theta/2)$, where $v_0(=c/\lambda_0)$ is the frequency reference of the laser.

In a usual configuration for measuring gas density, to keep the measurement unaffected by the fluctuation in laser energy from shot to shot, a reference measurement of the laser energy is implemented by recording a part of the signal or the laser light. The solution for a reference adopted in this work is a secondary measurement volume located in a glass cell containing a gas with known pressure, temperature, and composition. By normalization with the cell signal total intensity $A_0$ the laser energy fluctuations from pulse to pulse during the measurement are minimized. Additionally, the measured cell parameters provide simultaneously a reference for known gas density, temperature, and velocity (zero for stagnant gas). Integrating over the solid angle of the collecting optics and rewriting in dimensionless quantities, Eq. (7) becomes $\rho_m = C_2(A_m/A_0)/(\sigma/m_m)$, where $A_mA_0$ is the non-dimensional integral of the signal, $\rho_m$ is the gas density normalized by $\rho_{air}$, and $\sigma = \Sigma_i^{Ni}(\chi_i\sigma_i)/\sigma_{air}$ is the non-dimensional scattering cross section of the gas weighted by the molar fraction of species $\chi_i$. The constant $C_2$ is found from simultaneous measurements of known gas properties in the cell ($N_2$) and in air at the measurement volume.

The total measured signal is computed by integrating the spectral fit function (solid line in FIG. 3 minus the reference Lorentzian function). For $y<<1$, the integral can be approximated by (assuming a Gaussian function) the maximum spectral intensity multiplied by full-width half maximum and $(2\pi)^{1/2}$.

FIG. 4 shows the profiles of measured quantities in the Hencken burner flame at equivalence ratio of $\phi=1.0$ (line X) and $\phi=0.5$ (line Y), relative to the known quantities in the cell (Z trace). Data is extracted from single-shot interferograms using Gaussian and Lorentzian fit functions as approximation for the Rayleigh and laser spectra. FIG. 4(a) shows the normalized spectral bandwidth $W_m$ measured at the flame location. The normalization factor is the spectral width $W_0$ obtained at this location in air at room temperature (~293.5 K). The width obtained in the $N_2$ cell, about 9% narrower than the width measured in the air, can also be used for reference. FIG. 4(b) shows the integral of the signal intensity measured at the flame location, relative to the integral of the signal obtained in the cell, corrected for the cell signal intensity relative to the flame signal intensity. The core flame cross section, where the flame properties are almost uniform, is about 20 mm×20 mm. The measurement volume was scanned along a line from one side to the other over the center of the burner (shown in the inset image of FIG. 4) in a plane situated at about 38.5 mm above the burner surface (similar measurements of rotational-vibrational temperature using CARS were performed by Hancock ("Nitrogen and Hydrogen CARS Temperature Measurements in a Hydrogen/Air Flame Using a Near-Adiabatic Flat-Flame Burner," Combustion and Flame, Vol. 109, No. 3, 1997, pp. 323-331)). The Doppler shift frequency obtained in flame at equivalence ratio of $\phi=0.5$ relative to the maximum measurable frequency (defined by the interferometer) is shown in FIG. 4(c). The simultaneous properties measured in the reference cell are plotted with red symbols. The normalization factors for the cell properties in FIG. 4(a) and FIG. 4(b) are the measured cell properties, the spectral width and the integral of the signal in the cell at one atmosphere, respectively. The spatially resolved measurements of the relative spectral width show a slight flame asymmetry in this property as the measurement volume is scanned across the flame region (FIG. 4(a)). This is evidenced more at higher flame temperatures (blue) than at intermediate ones although in both cases they correlate approximately with the position of the burner nozzles revealing the discrete (flamelet) structure of the flame. In the core region of the flame the measured average temperature is 2323 K±415 K (±one standard deviation) on the left side and 2083 K 343 K on the right side of the axis of flame at $\phi=1.0$. These average values are about 2.2% and 12.4%, respectively, lower than predicted. The large standard deviation of the measurement is attributed partly to the variation with position (during the scan) in flame temperature and composition due to the flamelet structure and partly to random measurement error. At moderate temperatures (~$\phi=0.5$), when the flame is more uniform, this variation is smaller than 80 K. Because the measurements were not performed at a fixed location in the flame, the instrument random error in measuring temperature is not directly quantifiable at this time.

The measured density in air, and flame at $\phi=1$ are 1.23 kg/m$^3$+0.05 kg/m$^3$ and 0.13 kg/m$^3$±0.007 kg/m$^3$, respectively. These mean values are higher than predicted, by about 2.5% in room air and by about 4.5% at the flame. The higher-than-expected value of density in the flame suggests also a flame of lower temperature than predicted as well as measured from the spectral width.

Figure 5:
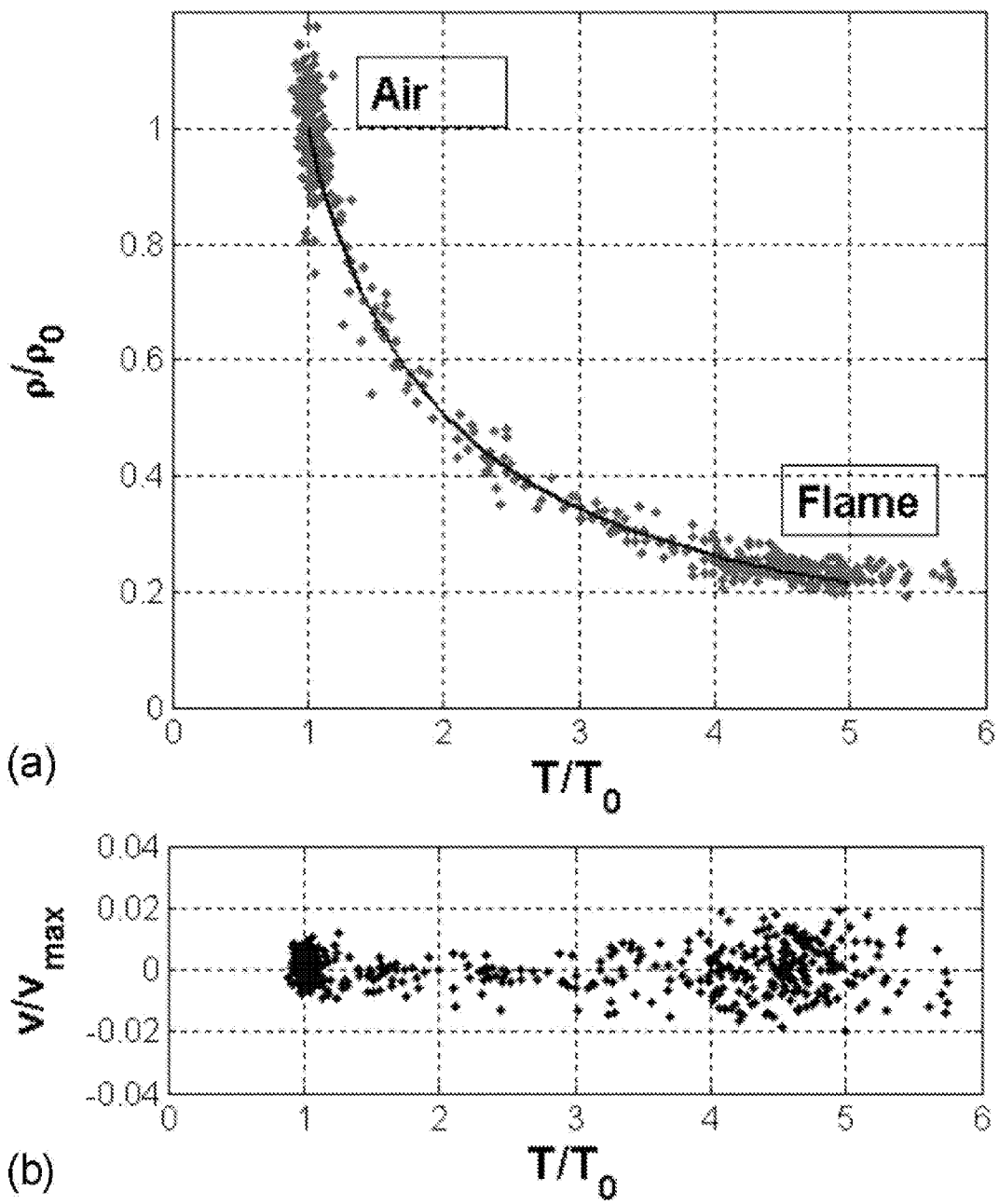

The gas density, and bulk velocity computed from spectral properties obtained in air and the flame (data shown in FIG. 4) during the full scan of the flame at $\phi=0.5$, are shown in FIG. 5 as a function of the computed temperature. The gas density and temperature are normalized with respect to the ambient air density (1.2 kg/m$^3$) and temperature (293.5 K), respectively. The velocity is normalized by the maximum measurable velocity (3 km/s) defined by the optical setup, i.e. the interferometer free spectral range.

As shown in FIG. 5(a), the measured gas density dependence on the measured translational temperature (blue symbols), agrees very well with the perfect gas law (solid curve) computed for this case. In this computation the gas temperature and composition is assumed to be only a function of $\phi$ so the gas molecular weight can be inferred as a function of the temperature outside of the flame core where $\phi$ is unknown. The measured velocity dependence on the flame temperature is shown in FIG. 5(b). The rms (root mean square) variations that include true innate instrument errors and spatial and temporal fluctuations of the flow. As expected, the mean velocity is near zero, and the rms fluctuations (±one standard deviation) of velocity increases with increasing temperature from about 11 m/s at the room temperature (and in the cell) to about 27 m/s in the flame core (and increases to 39 m/s at $\phi=1$). It should be noted that this instrument was not intended to measure near-zero velocities, but rather supersonic/hypersonic ones (up to 3 km/s). Therefore the error of measuring near zero velocity is less than 1% of the dynamic range of the instrument. To accurately measure low velocity flows, a higher resolution interferometer (lower free spectral range) and a backward scattering direction (more sensitive to Doppler shift) could be selected.

To our knowledge, these high resolution temporal and spectral measurements of simultaneous gas translational temperature, velocity, and density using interferometric Rayleigh scattering are the first to be performed in $H_2$-air combustion flames.

Thus, the invention provides a non-intrusive optical diagnostic technique for temporally and spatially resolved measurements of multiple properties in reacting and non-reacting gases. The system employs a narrow-band pulsed laser source at 532 nm for simultaneous probing of molecules through elastic light scattering at two largely separated measurement locations, one of which is used for reference. The collected photons containing information from both measurement locations are analyzed spectrally with a planar Fabry-Perot interferometer. The reference measurement is located in a glass cell containing $N_2$ gas at low pressure (26.5 kPa) and room temperature (293.5 K). The measured cell spectral properties provide simultaneously a reference for known gas density (the spectral intensity), translational temperature (the spectral width), and supplementary near-zero gas velocity (zero average Doppler shift). Additionally, the cell spectral intensity provides the normalization factor for the laser energy fluctuations critical for the measurement of density. These spectral properties are used to calculate, by normalization, the gas density and translational temperature at the measurement location. The range of measurable temperatures and densities in gases is from cryogenic temperatures to about 2500 K (limited by the interferometer), and from 0.1 $kg/m^3$ to about 2 $kg/m^3$ (limited by the CCD dynamic range), respectively. The maximum dynamic range for measuring velocities is about ±1.5 km/s when no prior velocity direction is known, or about 3 km/s if the velocity direction is predictable.

In a laboratory demonstration, the measurement location is situated in a non-premixed near-adiabatic $H_2$-air Hencken burner flame at atmospheric pressure. The referenced measurements at different flame conditions compare favorably with the flame temperature and the gas density (up to the stoichiometric flame temperature of 2377 K) computed with the adiabatic flame theory. The random errors of measuring the flame properties, the translational temperature, velocity, and the gas density at the maximum measurable gas temperature, are estimated to less than about 17%, 39 m/s and 5%, respectively. These errors include the spatial and temporal variation of these properties across the flame.

The invention demonstrates simultaneous referencing (calibration) while performing measurements of velocity, density, and temperature with the interferometric Rayleigh scattering technique described here. In particular, the invention can be used for simultaneous multi-property turbulence studies of subsonic, supersonic, and hypersonic, nonreacting flows and predictable composition reacting flows in the range of temperatures, turbulence levels, and errors described here.

In another embodiment of the invention, an optical setup is implemented in which only one Rayleigh scattered light pulse (signal exp1) is collected from the measurement volume (mv1) by the L1 lens, and collimated and directed toward the PBS. Referring to FIG. 1, the PBS is used to inject the beam into a recycling optical path formed by the input mirror of the first interferometer F-Pi situated on the first optical axis and the input mirror of a second interferometer (E2—not shown) situated on a second optical axis perpendicular to the first optical axis. This interferometer replaces mirror $M_3$ and is adjusted such to reflect the signal received from PBS. A quarter-wave plate (QWP—not shown) located between the PBS and F-Pi rotates the polarization of the input beam exp1 to circular polarization.

The signal pulse polarization from mv1 is adjusted such that the PBS sends it toward the QWP and interferometer F-Pi first, and reflects it towards the QWP, PBS and the second interferometer (E2) afterwards. A small fraction of this light is transmitted through either interferometer, but most of it (depending on interferometer reflectivity) is reflected back into the opposite interferometer. In the usual arrangement, not containing the second interferometer this rejected light from F-Pi is lost. In the disclosed optical arrangement the reflected light by the F-Pi input mirror is reflected back on the optical axis again by the interferometer input mirror of the second interferometer. At the second reflection the QWP rotates the polarization to the initial input polarization and the remaining beam energy is lost on the first optical axis. This is demonstrated in Bivolaru, et al., "Multipoint Interferometric Rayleigh Scattering using Light Recirculation," AIAA-2008-3708, 26th AIAA AMT-GT Conference, Seattle, Wash., Jun. 23-26, 2008, using a mirror instead of a second interferometer (see also Bivolaru et al., U.S. Pat. No. 7,414,708). Optical means (not shown) directs the light passing through E2 toward L6 to generate a second interferogram.

In a further aspect, the interferometer F-Pi is selected for the maximum range of measurable velocities while the second one for a much lower range (or vice versa), e.g., with the free spectral range of 8 GHz (low spectral resolution) and 3.75 GHz (high spectral resolution), respectively. The interferometer F-PI is used to remove the ambiguity in the sign of the velocity being measured, while the second one measure it accurately. At higher temperatures this interferometer cannot be used due to the overlap of the consecutive interference orders, the second interferometer suffices. Similarly, at very low gas temperatures (<290 K) when the Rayleigh spectra are narrow, the second interferometer suffices. The dynamic range and accuracy of the instrument can be adjusted by selecting the free spectral ranges of the interferometers, depending on the application.

In a further aspect, for the disclosed implementation a second direct-viewing collecting optic (similar to lenses L1, L2 and L3) collects and collimates Rayleigh light (ref2) from a second measuring volume situated in a controlled environment, FIG. 1. The light polarization is adjusted and directed such that the PBS reflects it toward F-Pi. After one pass through the interferometer the reflected signal cannot be recovered and is lost. To avoid the overlap of spectra, the reference pattern of ref2 is rotated 90° in the image plane using the Dove prism DP. Therefore the interferograms generated by both interferometers, contain the spectra of exp1, ref1 (probing laser spectra), and ref2 (reference spectra), and the spectra of exp2 (the high resolution Rayleigh spectra) and ref1, respectively.

In another embodiment of the invention, a single direct-viewing optic is used to collect light from two (or more) largely-separated measurement volumes. One (or more) mirror(s) or equivalent optics placed in close proximity to the lens L1 location, receives and transmits (toward the lens) light from additional measurement volumes. One measurement volume is used for direct probing as in the new or prior art while the secondary measurement volumes are used for measurements of density, temperature, and velocity in conjunction with one or more reference cells, or known gas flows. An example of a density (velocity and temperature) reference cell layout is shown in FIG. 1; or by imaging optical fiber(s) that collect signal(s) from widely separated measurement or reference location(s). An example of an interferogram used to combine two signals, one directly from a measurement volume (vertical pattern), and one from an imaged optical fiber used for density reference (three semi-circular sectors) is shown in FIG. 6. The optical fiber collects light remotely from a density reference cell. The circular pattern is the interferogram of the laser light used for frequency reference.

FIG. 6 is for a combined single-shot interferogram of signal, frequency reference, and density reference from an optical fiber. The single shot image shows an interferogram of a signal collected from the measurement volume, an interferogram of signal from a secondary measurement volume used as density reference, and an interferogram of the probing laser light used as a frequency reference. Thus, a single-shot interferogram is provided which combines a signal from a direct view optic as described previously, a frequency reference, and a density reference from an optical fiber.

In another embodiment of the invention shown in FIG. 7, the output fringe pattern of both interferometers are optically combined in a single beam and imaged onto a single high-sensitivity CCD camera. FIG. 7 shows the instantaneous image containing two interferograms of different spectral resolutions. A first interferogram 220 is shown having a free spectral range (FSR) of 3.75 GHz (F-Pi). A second interferogram 224 is shown having an FSR of 8 GHz (E2). The horizontal pattern 222 shows the additional non-spectrally resolved density signal delivered parallel with exp1 from the measurement volume. The vertical pattern 228 shows the spectrally resolved signal from the cell for referencing the density measurement (ref2). The frequency reference patterns (ref1) 226 are also shown. This provides better accuracy at lower velocities while preserving a large dynamic range. And, eliminates the Doppler shift sign ambiguity at higher velocities.

In another embodiment of the invention, the signal is further increased by increasing the laser energy deposited at the measurement volume without inducing the gas breakdown. A laser sheet or an elliptical beam at its focus allow more energy to be deposited in the flow, resulting in larger Rayleigh signal intensity if viewed from a parallel direction and more accurate measurements, at the cost of reduced spatial resolution in the other dimension. This can be achieved by tilting the focusing lens $L_1$ slightly (5-30 degrees) thereby introducing astigmatism, by using a combination of cylindrical and spherical lenses, or by a pair of anamorphic prisms or similar to generate a laser sheet.

In another embodiment of the instrument a laser sheet generated by tilted lens $L_1$ is viewed from a perpendicular direction such to permit two-dimensional measurements of parameters without decreasing the equivalent signal obtained from a single circular cross-section beam.

The following references are incorporated herein by reference. Drummond, J. P., Danehy, P. M., Bivolaru, D., Gaffney, Jr. R. L., Tedder, S. A., and Cutler, A. D., "Supersonic combustion research at NASA, 2007 Fall Technical Meeting," Eastern States Section of the Combustion Institute, University of Virginia, Oct. 21-24, 2007; Also, Drummond, J. P., et al., "Development of Methods to Predict the Effects of Test Media in Ground-Based Propulsion Testing," NASA/TM-2009-215766, 2009.

Baurle, R. A., "Modeling of High Speed Reacting Flows: Established Practices and Future Challenges," AIAA-2004-0267, 42th Aerospace Sciences Meeting, Reno, Nev., Jan. 5-8, 2004.

Cutler, A. D., Magnotti, G., Baurle, R. A., Bivolaru, D., Tedder, S. A., Danehy, P. M., Weikl, M. C., Beyrau, F., and Seeger, T., "Development of Supersonic Combustion Experiments for CFD Modeling", AIAA Paper 2007-0978, 45th AIAA Aerospace Sciences Meeting and Exhibit, Reno, Nev., Jan. 8-11, 2007.

Farassat, F., Doty, M. J., and Hunter, C. A., "The Acoustic Analogy—A Powerful Tool in Aeroacoustics with Emphasis on Jet Noise Prediction," AIAA Paper No. 2004-2872, Presented at 10th AIAA/CEAS Aeroacoustics Conference, Manchester, United Kingdom, May 10-12, 2004.

Eckbreth, A., "Laser Diagnostics for Combustion Temperature and Species." Combustion Science and technology Series, Vol. 3, 2nd ed., Gordon & Breach Publishers, Taylor & Francis Books, Inc., New York, N.Y., 1996.

Miles, R. B., Lempert, W. R., and Forkey, J. N., "Laser Rayleigh Scattering," Measurement Science and Technology, Vol. 12, 2001, pp. 33-51.

Bivolaru, D., Danehy, P. M., Gaffney, Jr. R. L., and Cutler, A. D., "Direct-View Multi-Point Two-Component Interferometric Rayleigh Scattering Velocimeter," AIAA-2008-0236, 46th Aerospace Sciences Meeting, Reno, Nev., Jan. 9-12, 2008.

O'Byrne, S., Danehy, P. M., Cutler, A. D., Tedder, S. A., "Dual-Pump Coherent Anti-Stokes Raman Scattering Measurements in a Supersonic Combustor," AIAA Journal, Vol. 45, No. 4, 2007, pp. 922-933.

Danehy, P. M., Magnotti, G., Bivolaru, D., Tedder, S., and Cutler, A. D., "Simultaneous Temperature and Velocity Measurements in a Large-scale, Supersonic, Heated Jet," Paper 1193, 55th JANNAF Propulsion Meeting, Boston, Mass., May 12-16, 2008. Also, D. Bivolaru, P. M. Danehy, and A. D. Cutler, "Simultaneous CARS and Interferometric Rayleigh Scattering," Review of Scientific instruments (to be published).

Bivolaru, D., Lee, J. W., Jones, S. B., Tedder, S., Danehy, P. M., Weikl, M. C., Magnotti, G., and Cutler, A. D., "Mobile Rayleigh—CARS Instrument for Simultaneous Spectroscopic Measurement of Multiple Properties in Gaseous Flows," 22nd International Congress on Instrumentation in Aerospace Simulations Facilities (ICIASF), Monterey, Calif., June, 2007. See also, Bivolaru, D, Danehy, P. M., Grinstead, K. D., Jr., Tedder, S., and Cutler, A. D., "Simultaneous CARS and Interferometric Rayleigh Scattering," AIAA-2006-2968, 25th AIAA Aerodynamic Measurement Technology and Ground Testing Conference, San Francisco, Calif., Jun. 5-8, 2006.

Bivolaru, D., Danehy, P. M., Lee, J. W., "Interferometric Rayleigh Scattering Measurement System," NASA, Washington, D.C., U.S. Pat. No. 7,414,708, Aug. 18, 2008.

Bivolaru, D. Danehy, P. M., Cutler, A. D., "Multipoint Inteferometric Rayleigh Scattering using Light Recirculation," Paper Number 2008-3708, 26th AIAA Aerodynamic Measurement Technology and Ground Testing Conference, Seattle, Wash. Jun. 23-26, 2008.

Yip, S. J., "Rayleigh Scattering from Diluted Gases," Acoust. Soc. Am. 49, 941-949 (1971).

Cattolica, R., Robeen, and Talbot, L., "The Interpretation of Spectral Structure of Rayleigh Scattered light from Combustion Gases," AIAA-1976-0031, 14th Aerospace Sciences Meeting, Washington, D.C., Jan. 26-28. 1976.

Pitz, R. W., Cattolica, R., Robben, F., Talbot, L., "Temperature and Density in Hydrogen-Air Flame From Rayleigh Scattering," Combustion and Flame, 27, 313-320 (1976).

Dibble, R. W., Starner, S. H., Masry, A. R., and Barlow, R. S., "An Improved Method of Data Acquisition and Reduction for Laser Raman-Rayleigh and Fluorescence Scattering from Multispecies," Appl. Phys. B, Vol. 51, No. 1, 1990, pp. 39-43.

Seasholtz, R. G., Zupanc, F. J., and Schneider, S. J., "Spectrally resolved Rayleigh scattering diagnostic for hydrogen-oxygen rocket plume studies," J. Propulsion Power, Vol 8, No. 5, 1992, pp. 935-942.

Young, A. T., and Kattawar, G. W., "Rayleigh Scattering Line Profiles," Applied Optics, Vol. 22, No. 23, 1983, pp. 3668-3670.

Bivolaru, D., Danehy, P. M., and Cutler, A. D., "Dual-cavity Rayleigh Scattering Measurement System," The George Washington University, Washington, D.C., U.S. Provisional patent application, No. 61/346,599, May 20, 2010.

Matthews, S. C., "Tilted Lens Imager in a Laser Amplifier/Oscillator and Method Utilizing Same," Hughes Aircraft Co., Los Angeles, Calif., U.S. Pat. No. 5,228,051, Jul. 13, 1993.

Gordon, S., and McBride, B. J., "Computer Program for Calculation of Complex Chemical Equilibrium Compositions, Rocket Performance, Incident and Reflected Shocks, and Chapman-Jouguet Detonations," NASA Report: SP-273, 1976.

Hancock, R. D., Bertagnolli, K. E., Lucht, R. P., "Nitrogen and Hydrogen CARS Temperature Measurements in a Hydrogen/Air Flame Using a Near-Adiabatic Flat-Flame Burner," Combustion and Flame, Vol. 109, No. 3, 1997, pp. 323-331.

The description and drawings of the present invention provided in the paper should be considered as illustrative only of the principles of the invention. The invention may be configured in a variety of size, shapes, and optical elements, and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

The invention claimed is:

1. A system for analyzing properties of gaseous media, comprising:
   a laser source providing a narrow-band pulsed laser which probes a location in the gaseous media and a reference location;
   a first optical element collecting scattered light from the gaseous media;
   a second optical element collecting scattered reference light from the reference location; and,
   a beam combiner optically mixing the scattered light collected by said first optical element with an unscattered light reference and the scattered reference light by said second optical element.

2. The system of claim 1, further comprising an interferometer receiving the mixed laser from said beam combiner.

3. The system of claim 2, further comprising a CCD camera for imaging the light from said interferometer.

4. The system of claim 3, further comprising a processor for analyzing the light from said interferometer to identify properties of the gaseous media.

5. The system of claim 4, wherein the system operates in real time to provide a diagnostic of gaseous media flows.

6. The system of claim 1, wherein the system operates in a range of temperatures, velocities, and gaseous media densities.

7. The system of claim 1, wherein the gaseous media is in the form of clusters of molecules (Mie scattering).

8. A system for spatially and temporally resolving multiple parameters of a gaseous media sample, the system comprising:
   a probing laser source providing a narrow-band pulsed laser source;
   a first optical element for focusing the laser on the gaseous sample;
   a second optical element collecting and collimating scattered light from a gaseous sample;
   a first beam reducer/expander reducing a diameter of the collected and collimated scattered light from the gaseous sample;
   a polarization dependent beam combiner;
   a first mirror directing the scattered light from said beam reducer/expander to said beam combiner;
   a third optical element collecting and re-collimating the laser passing through the gaseous sample;
   a second mirror directing the laser from said third optical element;
   a fourth optical element focusing the recovered and collimated laser on a reference measurement volume with known gaseous media properties;
   a second beam reducer/expander reducing the diameter of the scattered light received from the second optical element;
   a third mirror directing the scattered reference light from said second beam reducer/expander to said beam combiner, whereby said beam combiner optically mixes the scattered light from said first mirror with an unscattered light used for frequency referencing, and with the scattered reference light from said third mirror; and,
   a first Fabry-Perot interferometer receiving the mixed light signals from said beam combiner.

9. The system of claim 8, wherein the unscattered reference light passes through said third mirror toward said beam combiner.

10. The system of claim 8, wherein said first, second, third, and fourth optical elements each comprise a lens or a combination of lenses.

11. The system of claim 8, wherein said first and second beam reducer/expanders each comprise two lenses.

12. The system of claim 8, wherein the said system probes one location in a gaseous media using simultaneously two interferometers in a signal recycling configuration, the signal recycling configuration comprising:
   wherein said third optical element comprises a second Fabry-Perot interferometer receiving the light signals from the said beam combiner, wherein the second Fabry-Perot interferometer is adjusted perpendicular to an optical axis; and,
   a quarter-wave plate located between the beam combiner and the first Fabry-Perot interferometer, wherein the said quarter-wave plate modifies linear polarization of an incoming light beam to circular polarization.

* * * * *